United States Patent
Ishihara et al.

(10) Patent No.: US 10,945,956 B2
(45) Date of Patent: Mar. 16, 2021

(54) BIODEGRADABLE COMPOUND, LIPID PARTICLES, COMPOSITION AND KIT COMPRISING LIPID PARTICLES

(71) Applicant: KABUSHIKI KAISHA TOSHIBA, Minato-ku (JP)

(72) Inventors: Mitsuko Ishihara, Setagaya (JP); Eiichi Akahoshi, Shinagawa (JP); Katsuyuki Naito, Bunkyo (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 0 days.

(21) Appl. No.: 16/567,895

(22) Filed: Sep. 11, 2019

(65) Prior Publication Data
US 2020/0000723 A1   Jan. 2, 2020

Related U.S. Application Data

(63) Continuation of application No. PCT/JP2018/010376, filed on Mar. 16, 2018.

(51) Int. Cl.
*A61K 9/127* (2006.01)
*C07C 69/90* (2006.01)
*C12N 15/88* (2006.01)

(52) U.S. Cl.
CPC ............ *A61K 9/1272* (2013.01); *C07C 69/90* (2013.01); *C12N 15/88* (2013.01); *C12N 2310/141* (2013.01)

(58) Field of Classification Search
None
See application file for complete search history.

(56) References Cited

U.S. PATENT DOCUMENTS

| | | | |
|---|---|---|---|
| 4,218,234 | A | 8/1980 | Nadasy et al. |
| 4,486,391 | A | 12/1984 | Hashimoto |
| 5,534,499 | A | 7/1996 | Ansell |
| 5,820,873 | A | 10/1998 | Choi et al. |
| 5,885,613 | A | 3/1999 | Holland et al. |
| 6,180,669 | B1 | 1/2001 | Tamarkin |
| 6,320,017 | B1 | 11/2001 | Ansell |
| 6,350,431 | B1 | 2/2002 | Snow et al. |
| 7,030,265 | B2 | 4/2006 | Sin et al. |
| 7,166,745 | B1 | 1/2007 | Chu et al. |
| 8,969,353 | B2 | 3/2015 | Mahon et al. |
| 9,708,628 | B2 | 7/2017 | Tange et al. |
| 2019/0110986 | A1 | 4/2019 | Tange et al. |
| 2019/0175517 | A1 | 6/2019 | Martini et al. |

FOREIGN PATENT DOCUMENTS

| | | |
|---|---|---|
| CN | 104368011 B | 5/2017 |
| JP | 32 31 403 A1 | 3/1983 |
| JP | 2002-529439 A | 9/2002 |
| JP | 2004-517876 A | 6/2004 |
| JP | 2007-197855 A | 8/2007 |
| JP | 4699575 B2 | 6/2011 |
| JP | 2012-508235 A | 4/2012 |
| JP | 6093710 B2 | 3/2017 |
| WO | WO 2000/012454 A1 | 3/2000 |
| WO | WO 2013/073480 A1 | 5/2013 |
| WO | WO 2017/061150 A1 | 4/2017 |
| WO | WO 2017/100744 A1 | 6/2017 |
| WO | WO 2017/201349 A1 | 11/2017 |

OTHER PUBLICATIONS

International Search Report dated Jun. 12, 2018 in PCT/JP2018/010376 filed Mar. 16, 2018 (with English Translation of Categories of Cited Documents).

Hidetaka Akita, et al., "A Neutral Envelope-Type Nanoparticle Containing pH-Responsive and SS-Cleavable Lipid-Like Material as a Carrier for Plasmid DNA", Advanced Healthcare Materials, 2, 2013, 6 pages.

Hiroki Tanaka, et al., "Neutral Biodegradable lipid-envelope-type nanoparticle using vitamin A-Scaffold for nuclear targeting of plasmid DNA", Biomaterials, 35, 2014, 7 pages.

Kejin Zhuo, et al., "Modular degradable dendrimers enable small RNAs to extend survival in an aggressive liver cancer model", Proceedings of the National Academyof Sciences of the United States of America, 113 (3), 2016, pp. 520-525.

Prabhat Kumar, et al., "In-Plane modulated smectic Ä vs smectic 'A' lamellar structure in poly(ethyl or propyl ether imine) dendrimers", Polymer, 86, 2016, pp. 98-104.

*Primary Examiner* — Brian J Davis
(74) *Attorney, Agent, or Firm* — Oblon, McClelland, Maier & Neustadt, L.L.P.

(57) ABSTRACT

[Problem]
To provide a biodegradable compound having a structure decomposed in a cell, lipid particles containing the compound, and a pharmaceutical composition comprising the lipid particles.
[Solution]
The compound of the embodiment is represented by the formula (1): $P-[X-R-Y-R'-Q]_2$ (1). In the formula,
P is an alkyleneoxy having an ether bond,
X is a divalent linking group having a tertiary amine structure,
R is a divalent linking group,
R' is a single bond or a $C_1$ to $C_6$ alkylene, and
Q is a liposoluble vitamin residue, a sterol residue, or a $C_{12}$ to $C_{22}$ aliphatic hydrocarbon group. The structure of the compound contains at least one biodegradable group. From the compound in combination with other lipids such as a lipid capable of reducing aggregation, lipid particles can be formed. Further, the compound can be used for a pharmaceutical composition to deliver an activator into cells.

18 Claims, No Drawings

BIODEGRADABLE COMPOUND, LIPID PARTICLES, COMPOSITION AND KIT COMPRISING LIPID PARTICLES

CROSS REFERENCE TO RELATED APPLICATIONS

This application is based upon and claims the benefit of priority from the prior International Patent Application PCT/JP2018/010376, filed on Mar. 16, 2018, the entire contents of which are incorporated herein by reference.

TECHNICAL FIELD

The present disclosure relates to a biodegradable compound having a structure decomposed in a cell, and also to lipid particles containing the compound. The disclosure further relates to a composition and a kit which are used for delivering an activator such as a nucleic acid.

BACKGROUND ART

Many researches have been made on liposomes for the purpose of various disease treatments. Liposomes are lipid-made minute capsules with nanometer-order sizes. They can enclose therein various compounds and the like and also are excellent in biocompatibility, and hence are ideal material for selectively delivering therapeutic agents or activators to the aimed parts in living bodies. For that use, large unilamellar liposomes (LUV: large unilamellar vesicles) having a mean particle size of 100 nm or more are generally employed and various substances have been developed for the membrane of them.

The liposomes can be made of a single lipid. In that case, for example, a phospholipid having a head part and a hydrophobic part connected thereto is adopted as the lipid, so that molecules thereof assemble to form membranes and thereby to produce the minute capsules capable of enclosing activators or the like. However, in order that the liposomes can have favorable properties, they are generally made of a lipid mixture. The mixture comprises a combination of, for example, lipids having excellent biodegradability, inhibiting aggregation of the formed liposomes, having an effect of inhibiting leakage of enclosed substances, and having an effect of membrane fusion.

Those lipids are individually under research and development to further improve properties of the liposomes. For example, medical-use liposomes specialized for gene transfer are preferred to have high biodegradability, excellent biocompatibility, strong ability for gene transfer and low cytotoxicity, and accordingly lipids are preferably capable of forming those liposomes.

As the lipids described above, various compounds have been developed. However, living bodies to be treated may underlie various conditions and there are many diseases to be cured, and hence it is desired to increase kinds of lipids that can be selected according to the requirements. Further, there is a desire for lipids capable of forming liposomes having properties superior to those of conventional liposomes.

PRIOR ART DOCUMENTS

Patent Documents

[Patent document 1] Japanese Patent No. 6093710

DISCLOSURE OF INVENTION

Problem to be Solved by the Invention

In view of the above problem, embodiments of the present disclosure provide a new compound serving as a lipid capable of forming liposomes, and also provide lipid particles, a composition and a kit using the compound.

Means for Solving Problem

The compound according to an embodiment of the present disclosure is represented by the formula (1):

$$P\text{—}[X\text{—}R\text{—}Y\text{—}R'\text{-}Q]_2 \qquad (1)$$

wherein
P is an alkyleneoxy having one or more ether bonds in the main chain,
each X is independently a divalent linking group having a tertiary amine structure,
each R is independently a $C_1$ to $C_6$ alkylene,
each Y is independently a divalent linking group selected from the group consisting of single bond, ether bond, carboxylic ester bond, thiocarboxylic ester bond, thioester bond, amide bond, carbamate bond, and urea bond,
each R' is independently a single bond or a $C_1$ to $C_6$ alkylene, and
each Q is independently a liposoluble vitamin residue, a sterol residue, or a $C_{12}$ to $C_{22}$ aliphatic hydrocarbon group; provided that
the structure contains at least one biodegradable group selected from the group consisting of carboxylic ester bond, thiocarboxylic ester bond, dithiocarboxylic bond, amide bond, carbamate bond, carboxydioxy bond, and urea bond.

Also, the lipid particles according to another embodiment of the present disclosure is characterized by containing the above compound.

Further, the composition according to still another embodiment of the present disclosure is characterized by comprising the above lipid particles and a medium.

Furthermore, the kit according to yet another embodiment of the present disclosure is characterized by comprising the above lipid particles and a composition containing an introducer that introduces the above lipid particles into cells.

DETAILED DESCRIPTION

Definitions

Unless otherwise specified in the present specification, when numerical ranges are indicated using "to", they include both endpoints, and units thereof are common. For example, "10 to 25 mol %" means 10 mol % or more and 25 mol % or less.

In the present specification, the descriptions such as "$C_x$-$C_y$" and "$C_x$" mean the number of carbons in the molecule or substituent. For example, the term "$C_1$-$C_6$ alkyl" means an alkyl having 1 or more and 6 or less carbons. Also, in the present specification, "halogenated alkyl" refers to an alkyl in which one or more hydrogens in the alkyl are replaced with halogen. For example, "fluoroaryl" refers to an aryl in which one or more hydrogens in the aryl are replaced with fluorine.

Unless otherwise stated in the present specification, the term "alkyl" means a monovalent group obtained by eliminating one hydrogen from an arbitrary carbon of alkane. The "alkyl" includes a linear or branched alkyl. In addition, "cycloalkyl" means an alkyl having a cyclic structure. Moreover, an alkyl having a cyclic structure which contains a linear or branched alkyl substituent is also referred to as a "cycloalkyl".

Further, the term "alkenyl" means a monovalent group obtained by eliminating one hydrogen from an arbitrary carbon of alkene.

Furthermore, "hydrocarbon group" means a monovalent or divalent or more valent group which includes carbon and hydrogen, and optionally oxygen or nitrogen. Also, "aliphatic group" means a hydrocarbon group having no aromatic ring, and the structure thereof may be a linear, branched or cyclic one. The structure may be a combination of them. Unless otherwise specified, the aliphatic group may contain a hetero atom, such as, nitrogen, oxygen, sulfur, selenium, fluorine, chlorine or bromine. In addition, the aliphatic group may be monovalent or multivalent. Still further, "aromatic hydrocarbon group" is a group containing an aromatic ring and may have, if necessary, an aliphatic hydrocarbon group as a substituent.

[Biodegradable Lipid Compound]

The compound according to the embodiment is a substance suitably serving as a lipid for forming liposomes. It has a biodegradable group in its hydrophobic part, and hence functions as a biodegradable lipid compound. When applied to living bodies, it characteristically inhibits binding with proteins but shows low toxicity in cells. Further, the liposomes formed by this lipid compound have such non-cationic surfaces as reduce cytotoxicity enough to increase efficiency of introducing activators such as nucleic acids into cells.

The lipid compound is represented by the formula (1):

P—[X—R—Y—R'-Q]$_2$ (1).

In the formula,

P is an alkyleneoxy having one or more ether bonds in the main chain, each X is independently a divalent linking group selected from the group consisting of methylimino, 1,2-pyrrolidinediyl and 1,3-pyrrolidinediyl, each R is independently a $C_1$ to $C_6$ alkylene, each Y is independently a divalent linking group selected from the group consisting of single bond, ether bond, carboxylic ester bond, thiocarboxylic ester bond, thioester bond, amide bond, carbamate bond, and urea bond, each R' is independently a single bond or a $C_1$ to $C_6$ alkylene, and each Q is independently a liposoluble vitamin residue, a sterol residue, or a $C_{12}$ to $C_{22}$ aliphatic hydrocarbon group.

In addition, the above structure contains at least one biodegradable group selected from the group consisting of carboxylic ester bond, thiocarboxylic ester bond, thioester bond, amide bond, carbamate bond, carboxydioxy bond, and urea bond.

One of the characteristics of the compound according to the embodiment is that P in the formula (1) has an ether bond. In other words, P comprises at least one oxygen and the oxygen connects to two carbons. There are no particular restrictions on the number of oxygens contained in P, but preferably one or two oxygens are contained. Also, there are no particular restrictions on the number of carbons contained in P, but the hydrocarbon chain included in P preferably has 1 to 3 carbons and the total number of carbons in P is preferably 3 to 8. Examples of the preferred P are as follows:

—(CH$_2$)$_2$—O—(CH$_2$)$_2$—,
—(CH$_2$)$_2$—O—(CH$_2$)$_2$—O—(CH$_2$)$_2$—,
—(CH$_2$)$_2$—O—O—(CH$_2$)$_2$—,
—(CH$_2$)$_3$—O—(CH$_2$)$_2$—O—(CH$_2$)$_3$—, and
—(CH$_2$)$_2$—O—CH$_2$—O—(CH$_2$)$_2$—.

Because of the above structure, the compound molecule can be in a relatively free conformation. When the compound is used for producing liposomes, oxygens in the ether bonds form hydrogen bonds with incorporated nucleic acids or the like and, as a result, the enclosed amount thereof is increased.

Each X is a divalent linking group having a tertiary amine structure, and is preferably selected from the group consisting of methylimino, 1,2-pyrrolidinediyl and 1,3-pyrrolidinediyl. When the compound is used for producing liposomes, the tertiary amine structure provides high cell-membrane permeability.

In the formula (1), the R—Y—R'-Q moiety is a hydrophobic part. The hydrophobic part contains a biodegradable group, which is selected from the group consisting of carboxylic ester bond (—C(=O)—O—), thiocarboxylic ester bond (—C(=O)—S—), dithiocarboxylic ester bond (—C(=S)—S—), amide bond (—C(=O)—NH—), carbamate bond (—NH—C(=O)—O—), carboxydioxy bond (—O—C(=O)—O—), and urea bond (—NH—C(=O)—NH—).

The biodegradable group may be contained in the structure as Y, but it may be in Q. Specifically, when Q is a group derived from a liposoluble vitamin or a sterol, the group may contain a carboxylic ester group or the like. The biodegradable group may be contained in both of Y and Q, or either of them may contain two or more biodegradable groups.

Both of Y and R' are divalent groups linking R to Q.

Each Y is a divalent linking group selected from the group consisting of single bond, ether bond, carboxylic ester bond, thiocarboxylic ester bond, thioester bond, amide bond, carbamate bond, and urea bond. Each R' is a single bond or a $C_1$ to $C_6$ alkylene.

They need not comprise atoms and may be single bonds. However, when Q does not contain a biodegradable group, Y contains a biodegradable group.

Each Q is a liposoluble vitamin residue, a sterol residue, or a $C_{12}$ to $C_{22}$ aliphatic hydrocarbon group. Among them, a liposoluble vitamin residue and a sterol residue are preferred, and a liposoluble vitamin residue is more preferred.

The liposoluble vitamin residue is a group derived from a liposoluble vitamin. Examples of the liposoluble vitamin include: retinol, retinal, ergosterol, 7-dehydrocholesterol, calciferol, cholecalciferol, dihydroergocalciferol, dihydrotachysterol, tocopherol, and tocotrienol. Those liposoluble vitamins have hydroxy groups at their terminals. The liposoluble vitamin residue is, for example, a group formed by eliminating a hydrogen atom from one of those hydroxy groups. The residue may be a group derived from a liposoluble vitamin derivative. The liposoluble vitamin derivative is a compound in which hydroxy in a liposoluble vitamin is replaced with thiohydroxy, carboxy, thiocarboxy or dithocarboxy. The liposoluble vitamin residue has —S—, —C(=O)—O—, —C(=O)—S— or —C(=S)—S— at the terminal. It is particularly preferred for the liposoluble vitamin residue to be a group derived from retinol (vitamin A), tocopherol (vitamin E) or carboxylic acid derivatives thereof.

The sterol residue is a group derived from a sterol. Examples of the sterol include cholesterol, stigmasterol, β-sitosterol, lanosterol, and ergosterol. The sterol residue is, for example, a group formed by eliminating a hydrogen from the hydroxy in those sterols. The sterol residue may have the same terminal group as the above-described group derived from a liposoluble vitamin derivative. It is particularly preferred for the sterol residue to be a group derived from sterol, cholesterol, or carboxylic acid derivatives thereof.

The $C_{12}$ to $C_{22}$ aliphatic hydrocarbon group may be either linear or branched, and further may have a cyclic structure. The aliphatic hydrocarbon group may have unsaturated bonds. In that case, it generally has 6 or less, preferably 3 or less unsaturated bonds. The aliphatic hydrocarbon group contains preferably 12 to 18, more preferably 13 to 17 carbon atoms.

Among the above groups serving as Q, preferred are groups having UV-absorbing structures. Specifically, it is preferred to have a cyclohexane structure. If the compound contains a UV-absorbing structure, it becomes possible to reduce light-deterioration of lipid particles containing the compound as an ingredient and further, when the lipid particles need to be subjected to behavior analysis, the analysis can be easily carried out.

The compound of the formula (1) contains two [X—R—Y—R'-Q] units. Those Xs, Rs, Ys, R's and Qs are individually independent, and they may be the same as or different from each other. However, they are preferably the same so that the compound may have an objective structure.

Each part of the compound according to the embodiment has the structure described above. The compound of the embodiment preferably has a structure represented by one of the following formulas (1-01) to (1-12).

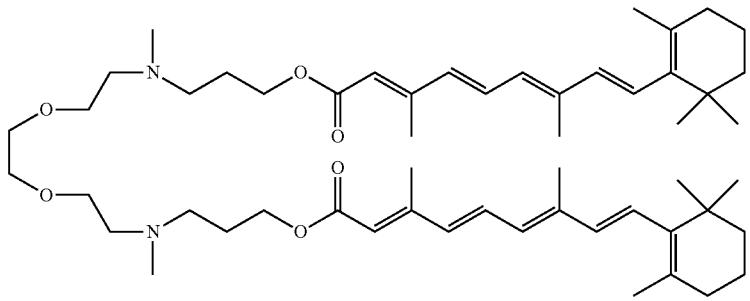

(1-01)

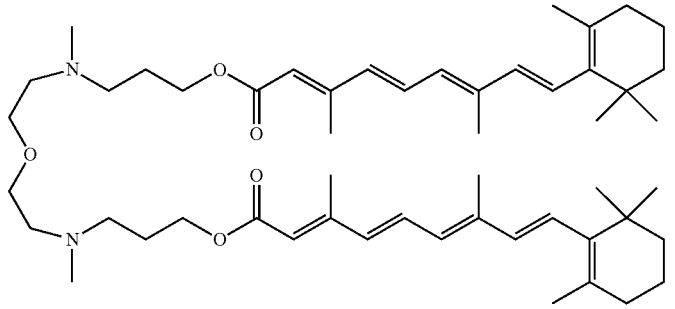

(1-02)

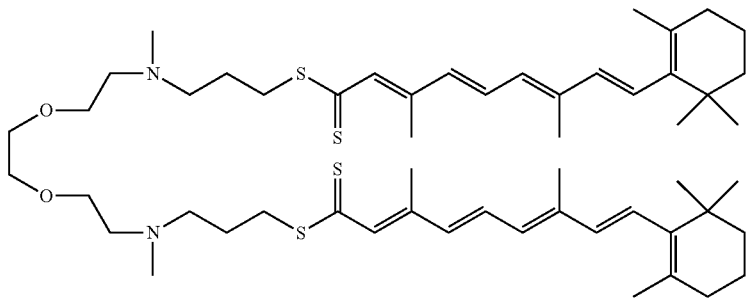

(1-03)

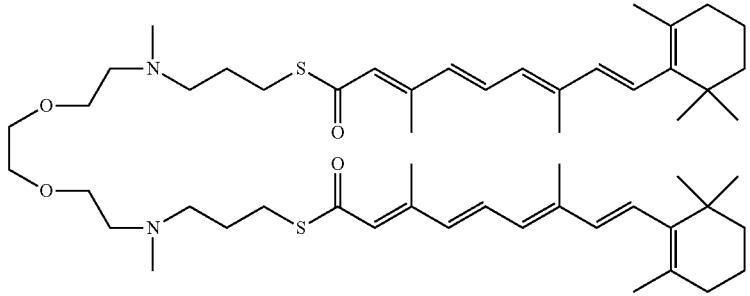

(1-04)

(1-05)
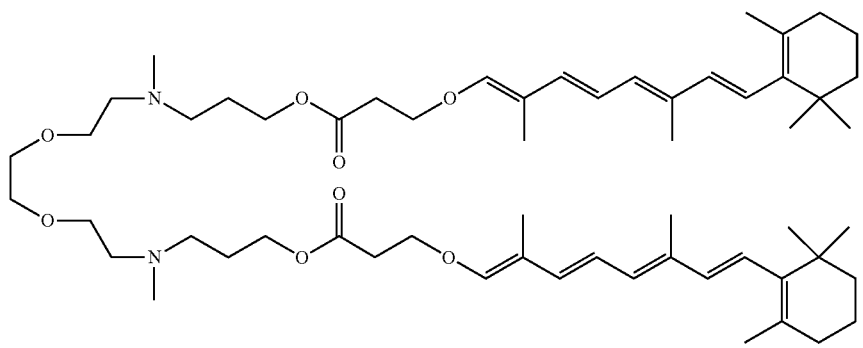
(1-06)
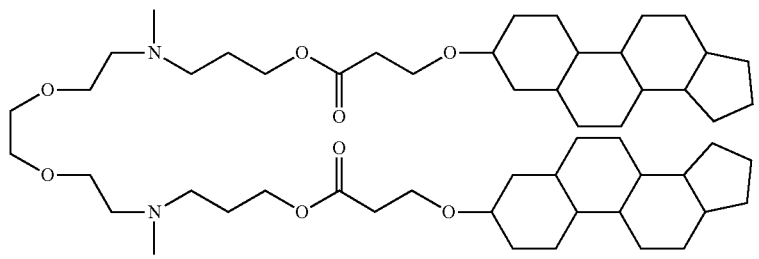
(1-07)
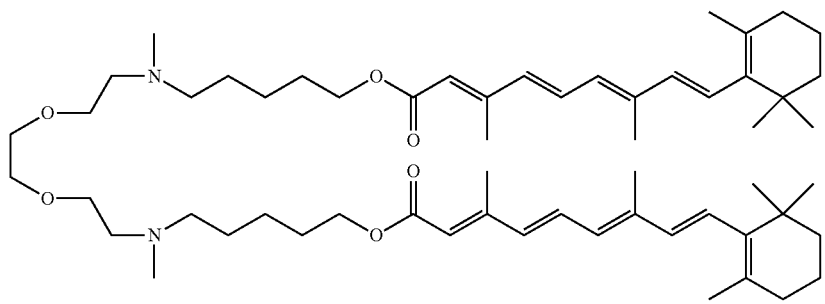
(1-08)
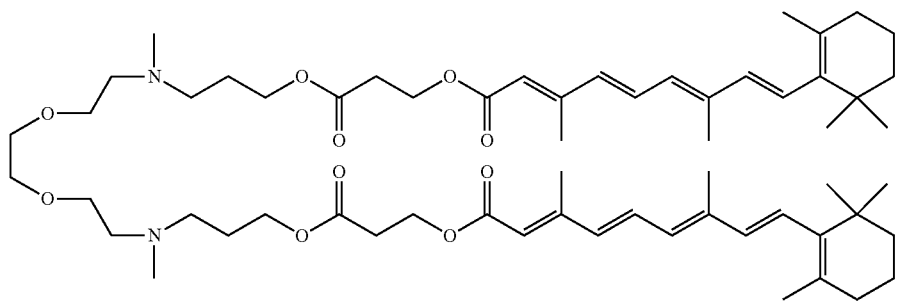
(1-09)
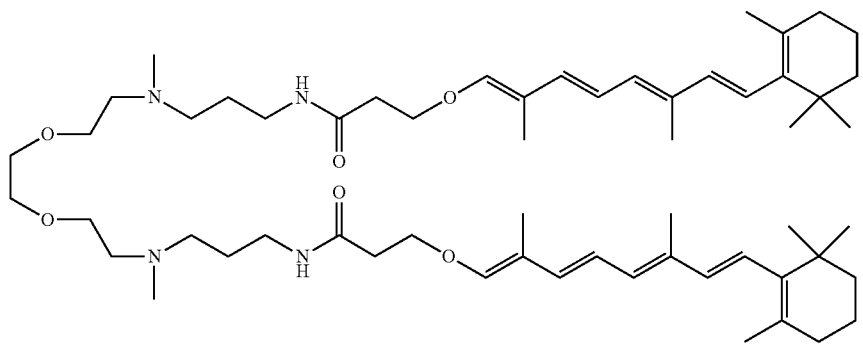

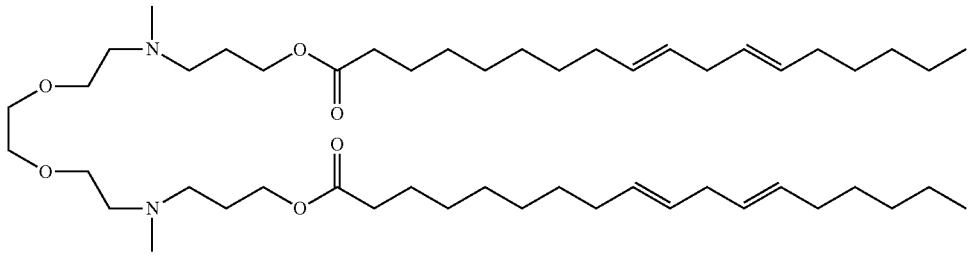
(1-10)
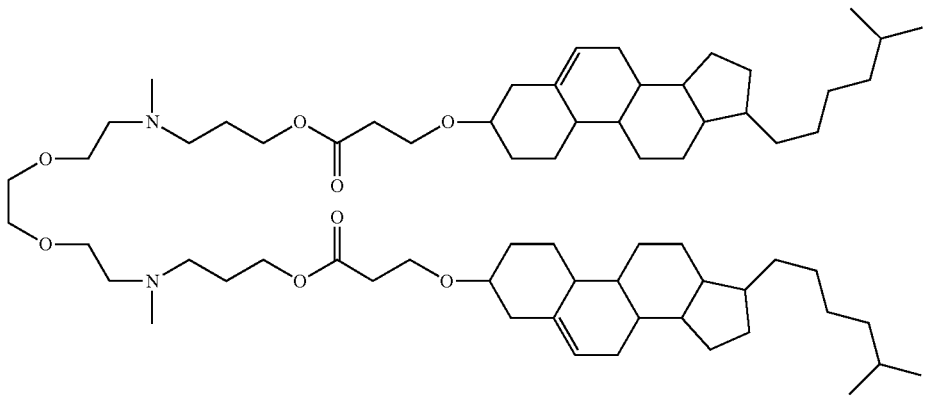
(1-11)
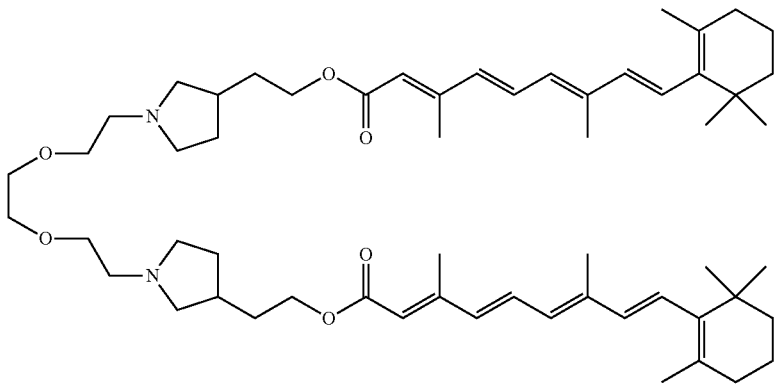
(1-12)
Among the above, the structures of (1-01) to (1-04) are particularly preferred because liposomes formed from them show excellent properties.
[Process for Producing the Compound]
The above compound can be produced, for example, according to the steps shown by the following chart.
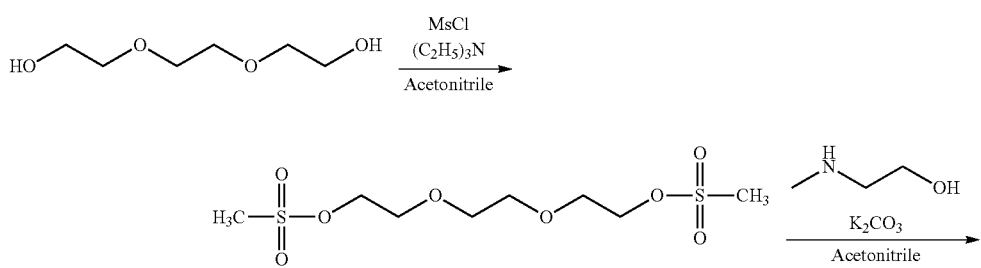
1

-continued

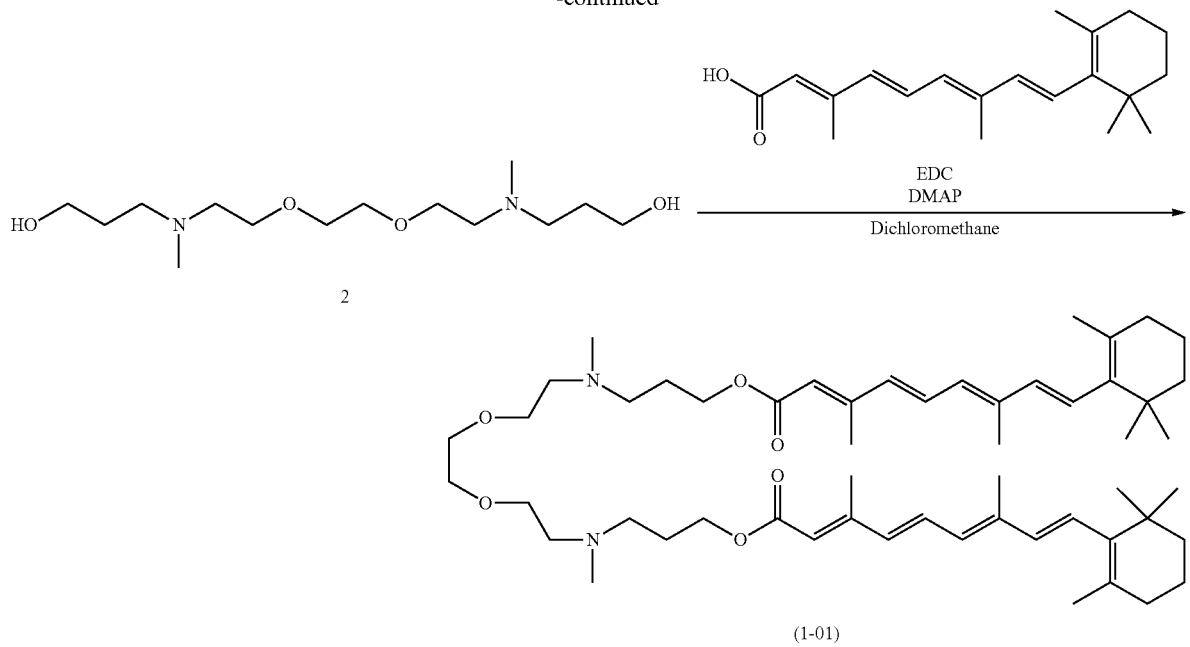

(1-01)

The production process shown above comprises fewer steps than that of conventional lipid compounds, and hence can realize highly efficient production.

[Lipid Particles]

The embodiment provides lipid particles. The lipid particles are typically liposomes, but not limited to them. For example, lipoplexes, which are liposomes complexed with nucleic acids or the like, are also included therein.

The liposomes may be either unilamellar or multilamellar.

The lipid particles according the embodiment contains the compound represented by the above formula (1), and preferably further contains a lipid forming a membrane and a lipid capable of reducing aggregation. Here, the "lipid forming a membrane" excludes the compound of the above formula (1) although the compound represented by the above formula (1) functions as a lipid forming a membrane.

As the lipid forming a membrane, any lipid can be adopted as long as it is generally used for liposomes. The lipid is preferably excellent in biodegradability.

Examples of the lipid forming a membrane include: diacyl phosphatidylcholine, diacyl phosphatidyl-ethanolamine, ceramide, sphingomyelin, dihydro-sphingomyelin, cephalin, and cerebroside. In the embodiment, the lipid forming a membrane is properly selected in consideration of sizes and stability of the aimed liposomes in living bodies. Among the above, diacyl phosphatidylcholine and diacyl phosphatidyl-ethanolamine are preferred. The acyl group contained in the lipid preferably has a hydrocarbon chain of 10 to 20 carbon atoms. The hydrocarbon chain may be either saturated or unsaturated.

As the lipid forming a membrane, various substances are known. Examples thereof include:
1,2-dioleoyl-sn-glycero-3-phosphoethanolamine (DOPE),
1,2-distearoyl-sn-glycero-3-phosphoethanolamine (DSPE),
1,2-dipalmitoyl-sn-glycero-3-phosphatidylcholine (DPPC),
1-palmitoyl-2-oleoyl-sn-glycero-3-phosphatidylcholine (POPC),
1,2-di-o-octadecyl-3-trimethylammoniumpropane (DOTMA),
1,2-dioleoyl-3-dimethylammoniumpropane (DODAP),
1,2-dimyristoyl-3-dimethylammoniumpropane (14:0 DAP),
1,2-dipalmitoyl-3-dimethylammoniumpropane (16:0 DAP),
1,2-distearoyl-3-dimethylammoniumpropane (18:0 DAP),
N-(4-carboxybenzyl)-N,N-dimethyl-2,3-bis(oleoyloxy)-propane (DOBAQ),
1,2-dioleoyl-3-trimethylammoniumpropane (DOTAP),
1,2-dioleoyl-sn-glycero-3-phosphochlorin (DOPC),
1,2-dilinoleoyl-sn-glycero-3-phosphochlorin (DLPC),
1,2-dioleoyl-sn-glycero-3-phospho-L-serine (DOPS), and cholesterol. Those lipids not only have a function of forming a membrane of liposomes but also can show an effect of membrane fusion.

The lipid capable of reducing aggregation used in the embodiment fulfills a function of including aggregation among the particles in preparation thereof. Various lipids having that function are known and any of them can be selected to use in the lipid particles of the embodiment. Examples thereof include: polyethylene glycol (PEG)-modified lipid, polyamide oligomer derived from ω-amino(oligoethylene glycol) alkanic acid monomer (U.S. Pat. No. 6,320,017), and mono-sialo ganglioside. More specifically, ATTA lipids such as ATTA8-DPSE disclosed in U.S. Pat. No. 6,320,017 and polyethylene glycol-lipid conjugates disclosed in U.S. Pat. Nos. 5,820,873, 5,534,499 and 5,885,613 are employable.

When the lipid particles are produced, the PEG-modified lipid can form anchoring lipid-moieties on the surface of the particles. Examples of the PEG-modified lipid include: PEG-modified phosphatidyl-ethanolamine, PEG-modified phosphatidic acid, PEG-ceramide conjugates (e.g., C14 PEG-Cer or C20 PEG-Cer disclosed in Japanese Patent No. 3920330), PEG-modified dialkylamine, PEG-modified 1,2-diacyl-oxypropane-3-amine, PEG-modified diacylglycerol (e.g., 1,2-dimyristoyl-sn-glycerol-methoxypolyethyenegly-col: PEG-DMG), and PEG-modified dialkylglycerol. Among them, PEG-modified diacylglycerol and PEG-modified dialkylglycerol are particularly preferred.

When bulky modifying groups such as PEG are bound to the surfaces of the lipid particles, they have influence on stability of the lipid particles or liposomes. For example, U.S. Pat. No. 5,820,873 describes that the stability of lipid particles depends on such characteristics of the PEG modifying lipid as the length and saturation degree of the acyl chain and the size of the bulky head group in the modifying lipid. Accordingly, those characteristics are controlled according to the aimed lipid particles. For example, it is possible to select a PEG modifying lipid having short modifying groups so that the lipid particles may disappear in a short time, and it is also possible to select one having long modifying groups so that the lipid particles may stay in plasma for a long time. As a result, it is often possible to improve delivery of lipid particles to the target tissue.

The lipid particles can furthermore contain other lipids, which can be freely selected from generally used ones. For example, in order to control the toxicity, relatively low-toxic lipids can be incorporated. Further, it is also possible to incorporate a lipid having a particular structure so as to introduce functional groups for combining the lipid particles with ligands.

Moreover, when the lipid particles are adopted as liposomes, they can contain a sterol, such as cholesterol, as a lipid for inhibiting leakage of the enclosed substance. It is further possible to couple the lipid particles with a target agent. In that case, the coupling method can be freely selected from known methods.

The lipids described above are combined to produce the lipid particles, and the blending ratio thereof are controlled according to the purpose and hence not particularly limited. However, the amounts of the lipids are generally as follows: the lipid compound represented by the formula (1): 10 to 75 mol %, the lipid forming a membrane: 25 to 80 mol %, and the lipid capable of reducing aggregation: 1 to 10 mol %. Further, the amounts preferred are as follows: the lipid compound represented by the formula (1): 10 to 50 mol %, the lipid forming a membrane: 47.5 to 80 mol %, and the lipid capable of reducing aggregation: 1 to 10 mol %, for example, 2.5 mol %. Here, it should be noted that the balance between the compound of the formula (1) and the membrane-forming lipid is important and the introduction of the activator cannot be enhanced by only either one of them. Accordingly, the blending ratio between the compound of the formula (1) and the membrane-forming lipid is preferably 1:0.5 to 1:9, more 1:1 to 1:2 by mole ratio.

The lipid particles of the embodiment can still further contain an activator. In the embodiment, "activator" means a substance that gives a specific effect to cells, issues, organs or specimens. The specific effect may be biological, physiological or cosmetic one. The lipid particles of the embodiment makes it possible to deliver various activators to the aimed parts in living bodies. The activator may be enclosed in the lipid particles, may be attached on the outer or inner surface thereof, or may be placed inside of the lipid layer.

Typical examples of the activator are nucleic acids. For example, the activator is selected from the group consisting of plasmid, oligonucleotide, polynucleotide, small interfering RNA (siRNA), microRNA (miRNA), DNA, aptamer, and ribozyme. In addition, it is also possible to adopt antisense oligonucleotide, antago-mir, aDNA, plasmid, ribosomal RNA (rRNA), transfer RNA (tRNA), small nuclear RNA (snRNA), or mRNA.

As the miRNA, a miRNA in which 17 to 25 nucleotide units are linked can be adopted. In a preferred embodiment, the nucleic acid is an oligonucleotide in which 15 to 50 or 20 to 30 nucleotide units are linked. The siRNA can, for example, comprise 16 to 30 nucleotide units and have a double-stranded region. In another embodiment, the nucleic acid is immune stimulating oligonucleotide, decoy oligonucleotide, super mir, miRNA mimic, or miRNA inhibitor. Here, "super mir" means a polymer or oligomer which is derived from single-, double- or partly double strands of RNA, DNA, both thereof or denatured one thereof, which has substantially the same nucleotide sequence as miRNA and which is antisense to the target. The "miRNA mimic" here means a group of molecules usable for the purpose of imitating the gene silencing ability of one or more miRNAs. Accordingly, the term "miRNA mimic" indicates a synthesized non-coding RNA capable of entering RNAi pathways and of controlling gene expression. (This means that miRNA cannot be obtained by purification of substances collected from sources of endogenous RNA.)

When nucleic acids are used in combination with the lipid particles, the form thereof is not particularly restricted. For example, they may be single-strand DNAs or RNAs, double-strand DNAs or RNAs, or DNA-RNA hybrids. Examples of the double-strand RNA include SiRNA. Examples of the single-strand nucleic acid include antisense oligonucleotide, ribozyme, miRNA, and triplehelix-forming oligonucleotide.

If containing a nucleic acid, the lipid particles of the embodiment can further contain a compound combinable with the nucleic acid. The compound is, for example, a basic protein or a basic peptide. Preferred examples thereof include protamine, histone, and salts thereof. Specifically, for example, when combined with histone or salts thereof, a nucleic acid molecule is folded therein. When combined with protamine or salts thereof, a nucleic acid molecule is rolled therein. Accordingly, those compounds are effective in enclosing the nucleic acid into the lipid particles.

The lipid particles of the embodiment can furthermore contain a compound controlling expression of the nucleic acid in cells. This compound is preferably incorporated because expression of nucleic acid in cells can be controlled so that cells to which liposomes are delivered may be visualized or led to cell death. Examples of the compound include retinoic acid, cyclic adenosine monophosphoric acid (cAMP), and ascorbic acid.

In addition, the lipid particles according to the embodiment may still further contain lipoprotein, apolipoprotein or the like.

As the activator, other therapeutic agents can be employed. Examples of the therapeutic agents include: peptides, polypeptides, cytokines, growth factors, apoptosis factors, differentiation inducers, cell surface receptors and ligands thereof, and hormones. Specifically, the therapeutic agents are, for example, anti-inflammatory compounds, antidepressants, stimulants, analgesics, antibiotics, contraceptives, antipyretics, vasodilators, angiogenesis inhibitors, cytovascular agents, signal transduction inhibitors, cardiovascular drugs, tumor drugs, hormones or steroids.

When used in combination with the lipid particles, the activator is preferably introduced into the particles at a high introduction rate. Also, cell death is preferably seldom caused by cytotoxicity depending on properties of the lipids. However, when nucleic acids are introduced by use of known lipid particles, the introduction rate is generally low and cell death is often caused by cytotoxicity. In contrast, if the lipid particles of the embodiment are adopted, the introduction rate of nucleic acids can be enhanced and the cell death can be reduced. Specifically, when known lipid particles are employed, the introduction rate is about 10% and the cell death is extrapolated to be 60 to 70%. On the other hand, when the lipid particles of the embodiment are employed, the introduction rate and the cell death are improved to be 70% or more and 30% or less, respectively.

The lipid particles of the embodiment can be produced in optional sizes according to the purposes. However, when employed for medical use, the lipid particles are generally in the form of nano-order size particles. Specifically, the lipid particles according to the embodiment have a mean particle size of generally 50 to 300 nm, preferably 50 to 200 nm. The size of the lipid particles can be controlled in any manner. For example, the particles can be subjected to ultrasonic treatment so as to reduce the sizes. Further, for the purpose of sizing the lipid particles, it is also possible to make the particles permeate a polycarbonate or ceramic membrane. Here, in the present embodiment, the mean size of the lipid particles can be measured, for example, with a Zetasizer according to dynamic light scattering method.

The lipid particles of the embodiment has an in-vivo half-life ($t_{1/2}$) of generally less than 3 hours, preferably less than 2 hours, more preferably less than 1 hour. Here, "in-vivo half-life" means a half-life in, for example, the liver, the spleen or the plasma. Since the lipid is made of the compound of the formula (1) having a biodegradable group, the lipid particles of the embodiment has, for example, less than 10% as short a half-life as particles of lipids having no biodegradable group.

[Process for Producing the Lipid Particles]

The lipid particles according to the embodiment can be produced in any known manner. Examples of known methods for producing lipid particles or liposomes include Bangham method, organic solvent extraction method, surfactant removal method, and freeze-thaw method. Those may be adopted. However, in another way, for example, the compound represented by the formula (1), the lipid forming a membrane and the lipid capable of reducing aggregation are added in an organic solvent such as an alcohol, and then an aqueous buffer is added therein so that the lipid particles can spontaneously form. In this process, the activator can be introduced into the lipid particles if incorporated in the aqueous buffer.

The lipid particles of the embodiment can be employed for delivering activators to cells. In particular, delivery to cells of activators such as nucleic acids is often adopted in various fields, for example, in genetic engineering, in production of recombinant proteins, and in medical technologies known as gene therapy and cytologic diagnosis.

[Composition]

The lipid particles according to the embodiment can be used in the form of a composition. For example, the composition comprises the lipid particles of the embodiment and a medium. That composition is applicable to medical use.

The medium can be optionally selected from known ones, and examples thereof include water, sodium chloride solution such as physiological saline, aqueous glycine solution, and buffer solution. In addition to those media, glycoproteins such as albumin, lipoproteins, apolipoproteins and globulin can be incorporated therein for the purpose of improving the stability.

The composition of the embodiment can be prepared in a standard manner. As the medium, physiological saline is normally adopted. When sodium chloride solution or other salt-containing medium is used in the composition, that medium is preferably added after the lipid particles are formed. Accordingly, in a normal manner, first the lipid particles and the activator such as a nucleic acid are combined and thereafter the obtained composition is then diluted with a pharmaceutically acceptable medium such as physiological saline.

The composition according to the embodiment can contain an auxiliary ingredient, if necessary. For example, when prepared for medical use, the composition can contain a pharmaceutically acceptable auxiliary ingredient, such as, pH adjuster, buffer agent, tonicity modifier, so as to be suited to physiological conditions. Examples of the auxiliary ingredient having that function include: sodium acetate, sodium lactate, sodium chloride, potassium chloride, and calcium chloride. The composition of the embodiment can further contain a lipid-protective agent for improving storage stability. The protective agent is, for example, a lipophilic free-radical quencher such as α-tocopherol, which prevents damage by free radicals; or a water-soluble chelator such as ferrioxamine, which prevents peroxidative damage of the lipid.

Further, the aforementioned activator can be added to the composition. The activator may be the same as or different from that combined with the lipid particles. Furthermore, the compound combinable with a nucleic acid and/or the compound controlling expression of nucleic acid can be added to the composition.

There are no particular restrictions on the amount of the lipid particles contained in the composition, but the amount thereof is generally 0.01 to 30 mass %, preferably 0.05 to 10 mass %. The concentration of the lipid particles can be properly selected according to the purpose.

The composition of the embodiment can be sterilized in known manners. The sterilized composition can be packaged as a pharmaceutical product capable of being directly dosed, but it also can be dried and then packaged. The dried composition is mixed with sterilized aqueous solution immediately before administration to prepare a solution capable of being dosed.

The composition according to the embodiment can be in a kit form. The kit of the embodiment comprises the aforementioned lipid particles and an introducer that introduces the lipid particles into cells, but the forms of them are not restricted. For example, the kit may comprise individual containers one of which holds a dispersion in which the lipid particles not combined with the activator is dispersed in a medium and another of which holds the activator; or otherwise the kit may comprise individual containers one of which holds the lipid particles in a dried form, another of which holds the activator and still another of which holds a medium. The lipid particles in a dispersion or in a dried form may be separated from the activator, and the lipid particles and the activator can be independently sold as individual products so that users can select the products according to their uses.

The kit can further comprise an agent used for introducing a nucleic acid.

[Way of Using Pharmaceutical Composition]

When the lipid particles of the embodiment is applied to medical uses, the composition can be employed for treatments of various human and animal diseases. For the purpose of that, the lipid particles are combined with therapeutic agents as the activators so as to deliver the agents to the target cells.

For example, various nucleic acids can be delivered to cells so that the cells may be brought into contact with the nucleic acids to prevent or treat diseases. Examples of the nucleic acids include: oligonucleotides, siRNAs, plasmids, antisenses, and ribozymes. The delivery of nucleic acids can be carried out either in vitro or in vivo.

As the method of in-vivo dosing of the pharmaceutical composition, preferred is parenteral administration, such as, intraarticular administration, intravenous administration, intraperitoneal administration, subcutaneous administration, or intramuscular administration. The intravenous or intraperitoneal administration of the pharmaceutical composition can be carried out by bolus injection.

Further, the pharmaceutical composition of the embodiment can be directly spread and applied on the aimed tissues so as to bring the tissues into contact with the composition. The composition also can be administered to the meninges or the like by drip injection, and still also can be administered by endoscopy.

In a particular embodiment, the treatment with the pharmaceutical composition is carried out at a physiological temperature (about 37° C.) for 1 to 24 hours, preferably 2 to 8 hours. There are no particular restrictions on the target cells of in-vitro administration. For example, they may be cells of vertebrates, invertebrates or plants. However, preferred are animal cells, more preferred are mammal cells, and particularly preferred are human cells.

EXAMPLES

[Synthesis Example 1] Synthesis of Compound (1-01)

According the aforementioned production process, a compound (1-01) was synthesized. Specific procedures thereof are described below.

Under an argon atmosphere, 5.00 g (33 mmol) of triethylene glycol, 14.39 mL (112 mmol) of triethylamine, and acetonitrile (50 mL) were placed in a 200-mL flask. After 7.97 mL (103 mmol) of methanesulfonyl chloride was dropwise added at 0° C., the mixture was stirred for 1 hour at room temperature. Subsequently, 10 mL of ethanol was dropwise added so as to treat unreacted methanesulfonyl chloride, and then the solution was filtrated and washed four times with 50 mL of dichloromethane. After dried with $Na_2SO_4$, the reaction solution was filtrated and concentrated to obtain an orange oily intermediate product 1 in an amount of 8.21 g (yield: 81%).

Thereafter, 842 mg (2.75 mmol) of the intermediate product 1, 950 mg (6.87 mmol) of $K_2CO_3$ and 15 mL of acetonitrile were placed in a 100-mL flask. After the mixture was stirred for 15 minutes at room temperature, 735 mg (8.258 mmol) of 3-(methylamino)-1-propanol was dropwise added. While the temperature was kept at 70° C., the mixture was stirred overnight. After the reaction solution was cooled, insolubles were removed by filtration. The filtrate was concentrated to obtain a crude product in an amount of 720 mg. The crude product was purified through a column chromatograph (15 g of NH silica-gel, developing solution: 50% hexane/chloroform), to obtain a pale yellow transparent oily intermediate product 2 in an amount of 348 mg (yield: 43%).

In a 30-mL eggplant flask, 300 mg (1.03 mmol) of the intermediate product 2 and 10 mL of dichloromethane were placed. After 770 mg (2.56 mmol) of retinoic acid, 50 mg (0.41 mmol) of 4-dimethylamino-pyridine and 590 mg (3.08 mmol) of 1-(3-dimethyl-aminopropyl)-3-ethylcarbodiimide hydrochloride were added, the mixture was stirred at room temperature overnight. Subsequently, the reaction solution was washed twice with 10 mL of water, and then dried with $Na_2SO_4$. The dried solution was filtrated and concentrated to obtain a crude product in an amount of 2.1 g. The crude product was purified through a column chromatograph (40 g of silica-gel, developing solution: 50% hexane/chloroform and chloroform), to obtain a deep orange oily compound 1-01 in an amount of 262 mg (yield: 29%).

Example 1

Solutions of vector DNA and a DNA condensing peptide were used to prepare a core complex comprising the vector DNA-DNA condensing peptide. The vector DNA employed here was a plasmid integrated with a cytomegalovirus early promoter/enhancer, a Nanoluc gene and a transcription terminator. The employed DNA condensing peptide was an oligopeptide derived from human protamine. The DNA condensing peptide solution (0.24 mg/ml, 10 mM HEPES, pH 5.4) in an amount of 10 µl was dispensed into a microtube (Proteosave SS 1.5 ml [trademark], manufactured by Sumitomo Bakelite Co., Limit.). While the dispensed peptide solution was being stirred with a vortex mixer (1500 rpm) (MAV-3500 [trademark], manufactured by Biosan Laboratories, Inc.), 200 µL of the vector DNA solution (0.15 mg/ml, 10 mM HEPES, pH 5.4) was dropwise added thereinto.

Liposomes enclosing the core complex were prepared according to an ethanol injection method. Into a microtube (Proteosave SS 1.5 ml [trademark], manufactured by Sumitomo Bakelite Co., Limit.), 50 µl of a lipid solution (the compound 1-01: DOTAP:cholesterol:DMG-PEG=5:3:1:0.3 mol) was dispensed. While the dispensed lipid solution was being stirred with a vortex mixer, 50 µl of the core complex was dropwise added thereinto. Thereafter, 400 µl of 10 mM HEPES (pH 5.4) was gently added to prepare liposomes enclosing the vector DNA. Further, 400 µl of 10 mM HEPES (pH 5.4) was added and gently mixed, and then the mixture was subjected to centrifugal buffer exchange and concentration by means of an ultrafiltration spin column (PT-1014 [trademark], manufactured by Apro Science Inc.), to prepare 100 µL of the core complex-enclosing liposomes (10 mM HEPES, pH 7.3).

Example 2

The procedure of Example 1 was repeated except for changing the lipid solution into a solution of the compound 1-01:PDME:cholesterol:DMG-PEG=5:3:1:0.3 mol, to prepare liposomes of Example 2.

Comparative Example 1

The procedure of Example 1 was repeated except for changing the lipid solution into a solution of the compound R-01:DOTAP:cholesterol:DMG-PEG=5:3:1:0.3 mol, to prepare liposomes of Comparative example 1.

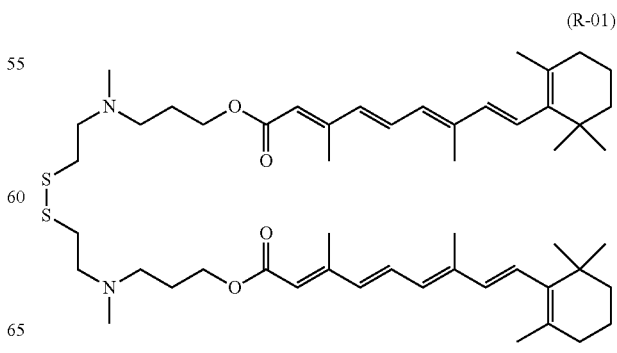

(R-01)

Comparative Example 2

The procedure of Example 1 was repeated except for changing the lipid solution into a solution of the compound R-01:PDME:cholesterol:DMG-PEG=5:3:1:0.3 mol, to prepare liposomes of Comparative example 1.

[Evaluation] Measurement of the Amount of DNA Enclosed in the Liposomes

The amount of DNA enclosed in the liposomes was measured by means of a Quant-iT PicoGreen dsDNA Assay Kit ([trademark], manufactured by Thermo Fisher Scientific Ltd.). The liposome solution of Example 1 in an amount of 5.0 µL was gently added to 95 µL of a Tris-EDTA buffer solution containing 0.1% Triton-X100, and the resultant suspended solution was left for 30 minutes at room temperature. Thereafter, the solution was well mixed with 100 µL of a PicoGreen solution diluted 200 times with the Tris-EDTA buffer solution. After the solution was left at room temperature for 5 minutes, the fluorescence intensity of the solution (excitation wavelength: 485 nm, emission wavelength: 530 nm) was measured with a microtiter plate reader (Mithras LB-940 [trademark], manufactured by Berthold Technologies GmbH & Co. KG). The DNA concentration was determined in reference to the standard curve produced with known concentrations of ADNA. From the obtained values, the amount of DNA enclosed in the liposomes was calculated as an amount per 1 mL of the solution (µgDNA/nnL). The results are shown in Table 1. It is thus revealed that the liposomes containing the compound 1-01 enclose DNA more than those containing the compound R-01.

[Evaluation] Measurement of the Vector DNA Introduction Rate by Liposomes

The amount of vector DNA introduced to cells by the liposomes (introduced amount) was quantified on the basis of expression of NLuc genes on vector DNA. For evaluating the expression of NLuc, emission thereof was measured with a microtiter plate reader (Mithras LB-940 [trademark], manufactured by Berthold Technologies GmbH & Co. KG). As the cells, human T cell leukemia cells: Jurkat (purchased from ATCC) were adopted. After 100 µL of the cell suspension ($1 \times 10^6$ cells/mL) was inoculated on a 96-well plate, 5 µL of the liposome solution prepared in Example 1 was added. Thereafter, the cells were incubated in an incubator at 37° C. for 48 hours under an atmosphere of 5% $CO_2$, and then enzyme activity of NLuc was measured. The measurement of NLuc enzyme activity was carried out by use of NanoGlo Luciferase Assay System ([trademark], manufactured by Promega Corporation) with a luminometer according to the manual attached to the kit. As shown in Table 1, it is revealed that the NLuc genes introduced into cells by the liposomes containing the compound 1-01 show expression more efficiently than those introduced by the liposomes containing the compound R-01.

[Table 1]

TABLE 1

| | Lipid ingredients of liposomes | Expression of vector DNA in cells (emission intensity: RLU) | Enclosed amount of vector DNA (µg DNA/mL) |
|---|---|---|---|
| Ex. 1 | compound 1-01 + DOTAP | 22238 | 9.4 |
| Ex. 2 | compound 1-01 + PDME | 4412 | 8.4 |
| Com. 1 | compound R-01 + DOTAP | — | 0.7 |
| Com. 2 | compound R-01 + PDME | 12 | 1.8 |

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fail within the scope and sprit of the invention.

The invention claimed is:

1. A compound represented by the formula (1):

$$P-[X-R-Y-R'-Q]_2 \qquad (1)$$

wherein

P is an alkyleneoxy having one or more ether bonds in the main chain, each X is independently a divalent linking group having a tertiary amine structure, each R is independently a $C_1$ to $C_6$ alkylene, each Y is independently a divalent linking group selected from the group consisting of single bond, ether bond, carboxylic ester bond, thiocarboxylic ester bond, thioester bond, amide bond, carbamate bond, and urea bond, each R' is independently a single bond or a $C_1$ to $C_6$ alkylene, and each Q is independently a liposoluble vitamin residue; provided that the structure contains at least one biodegradable group selected from the group consisting of carboxylic ester bond, thiocarboxylic ester bond, dithiocarboxylic bond, amide bond, carbamate bond, carboxydioxy bond, and urea bond.

2. The compound according to claim 1, wherein said P contains 3 to 8 carbons and 1 to 2 oxygens.

3. The compound according to claim 1, wherein said P contains only carbons and oxygens.

4. The compound according to claim 1, wherein each of said Xs is independently selected from the group consisting of methylimino, 1,2-pyrrolidinediyl and 1,3-pyrrolidinediyl.

5. The compound according to claim 1, wherein said liposoluble vitamin residue is a group derived from a liposoluble vitamin selected from the group consisting of retinol, retinal, ergosterol, 7-dehydrocholesterol, calciferol, cholecalciferol, dihydroergocalciferol, dihydrotachysterol, tocopherol, tocotrienol, and compounds in which hydroxy groups in those vitamins are replaced with thiohydroxy, carboxy, thiocarboxy or dithocarboxy.

6. The compound according to claim 1, wherein said Q has a cyclohexane structure.

7. The compound according to claim 1, represented by any of the following formulas (1-01) to (1-12):

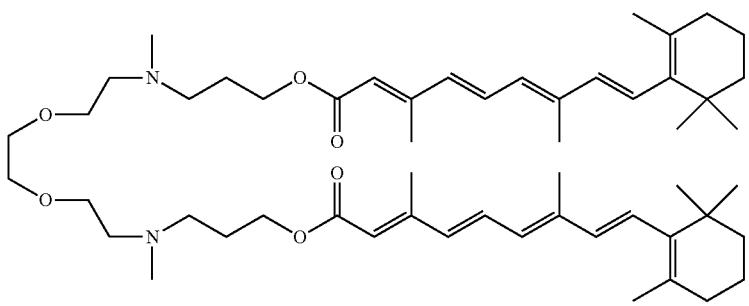
(1-01)
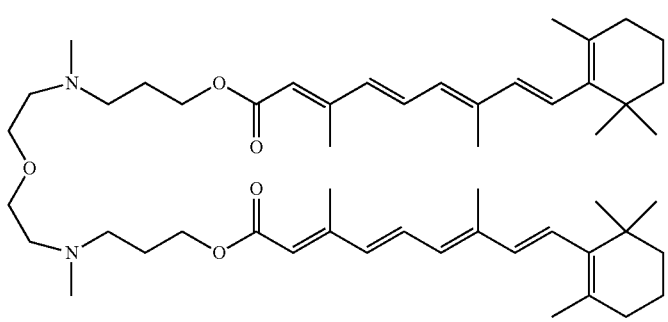
(1-02)
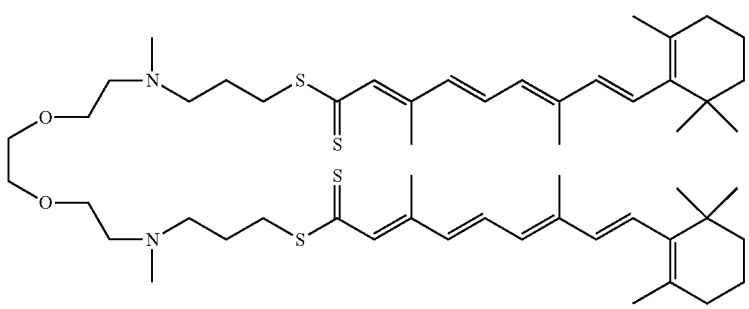
(1-03)
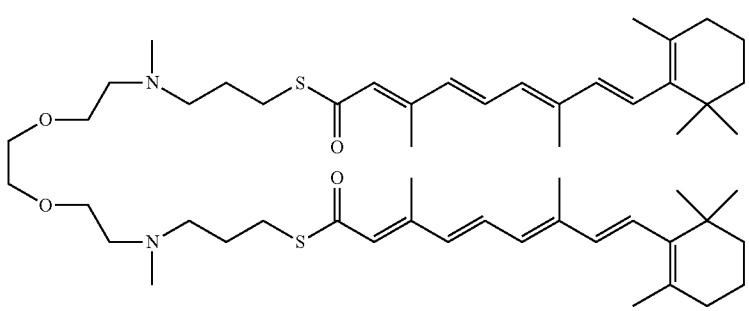
(1-04)
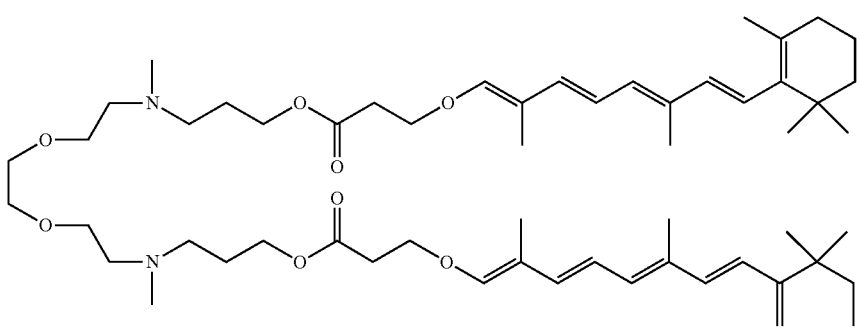
(1-05)

-continued (1-07)
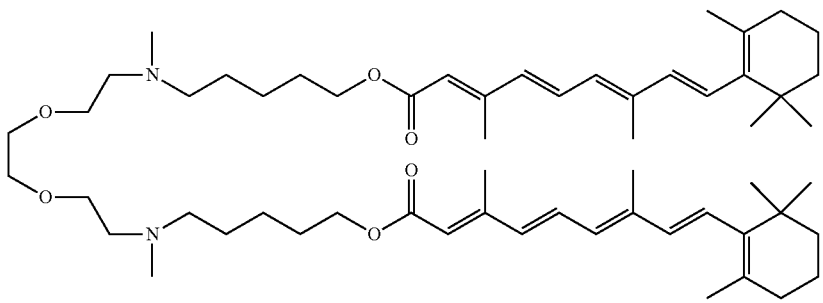

(1-08)
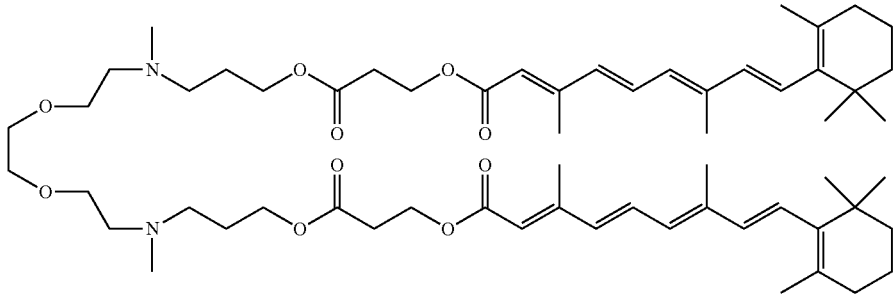

(1-09)
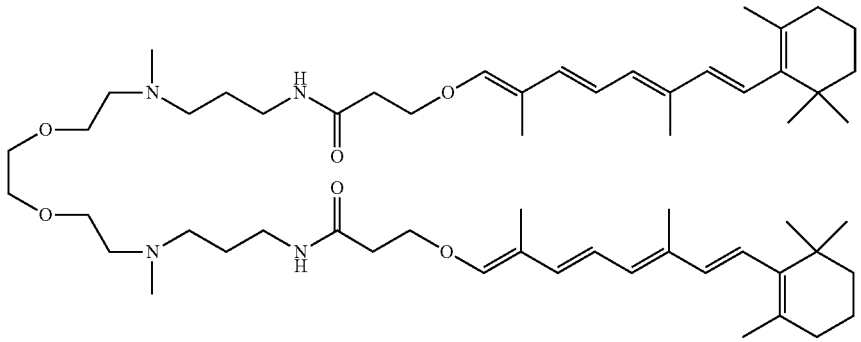

(1-12)
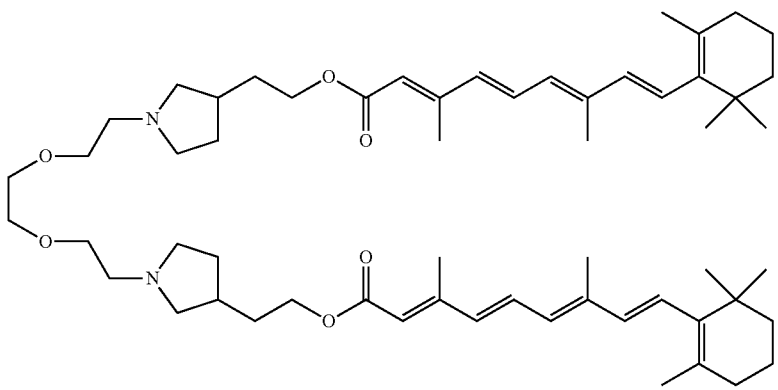

8. Lipid particles containing the compound according to claim 1.

9. The lipid particles according to claim 8, which further contains a lipid forming a membrane and a lipid capable of reducing aggregation.

10. The lipid particles according to claim 9, wherein said lipid forming a membrane is selected from the group consisting of 1,2-dioleoyl-sn-glycero-3-phosphoethanolamine (DOPE),
1,2-distearoyl-sn-glycero-3-phosphoethanolamine (DSPE),
1,2-dipalmitoyl-sn-glycero-3-phosphatidylcholine (DPPC),
1-palmitoyl-2-oleoyl-sn-glycero-3-phosphatidylcholine (POPC),
1,2-di-o-octadecyl-3-trimethylammoniumpropane (DOTMA),
1,2-dioleoyl-3-dimethylammoniumpropane (DODAP),
1,2-dimyristoyl-3-dimethylammoniumpropane (14:0 DAP),
1,2-dipalmitoyl-3-dimethylammoniumpropane (16:0 DAP), 1,2-distearoyl-3-dimethylammoniumpropane (18:0 DAP),
N-(4-carboxybenzyl)-N,N-dimethyl-2,3-bis(oleoyloxy)propane (DOBAQ),
1,2-dioleoyl-3-trimethylammoniumpropane (DOTAP),
1,2-dioleoyl-sn-glycero-3-phosphochlorin (DOPC),
1,2-dilinoleoyl-sn-glycero-3-phosphochlorin (DLPC),
1,2-dioleoyl-sn-glycero-3-phospho-L-serine (DOPS), and cholesterol; and
said lipid capable of reducing aggregation is a polyethylene glycol (PEG)-modified lipid.

11. The lipid particles according claim 8, which furthermore contains an activator.

12. The lipid particles according to claim 11, wherein said activator is a nucleic acid selected from the group consisting of plasmid, oligonucleotide, polynucleotide, siRNA, microRNA, DNA, mRNA, aptamer, and ribozyme.

13. The lipid particles according to claim 12, which further contains a compound combinable with the nucleic acid.

14. The lipid particles according to claim 13, wherein said compound combinable with the nucleic acid is a basic protein or a basic peptide.

15. The lipid particles according to claim 13, wherein said compound combinable with the nucleic acid is protamine or histone.

16. The lipid particles according to claim 13, which further contains a compound controlling expression of the nucleic acid in cells.

17. A composition comprising the lipid particles according to claim 8 and a medium.

18. A kit comprising the lipid particles according to claim 8 and a composition containing a medium that introduces said lipid particles into cells.

* * * * *

UNITED STATES PATENT AND TRADEMARK OFFICE
CERTIFICATE OF CORRECTION

PATENT NO. : 10,945,956 B2  Page 1 of 1
APPLICATION NO. : 16/567895
DATED : March 16, 2021
INVENTOR(S) : Mitsuko Ishihara et al.

It is certified that error appears in the above-identified patent and that said Letters Patent is hereby corrected as shown below:

In the Claims

Claim 7, formula (1-05) should read:

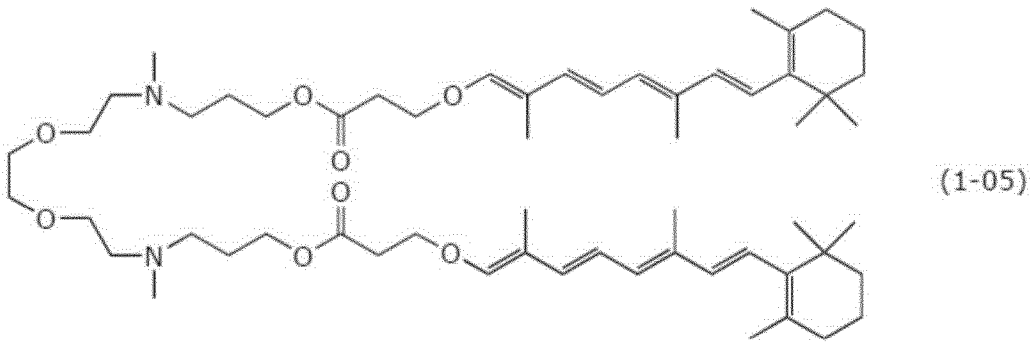

Signed and Sealed this
Nineteenth Day of April, 2022

Katherine Kelly Vidal
*Director of the United States Patent and Trademark Office*